(12) United States Patent
Faires

(10) Patent No.: US 7,621,462 B2
(45) Date of Patent: *Nov. 24, 2009

(54) ACTUATED AIR FRESHENER DISPENSER

(75) Inventor: Geoffrey Faires, Cave Creek, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/749,529

(22) Filed: May 16, 2007

(65) Prior Publication Data

US 2007/0267514 A1    Nov. 22, 2007

Related U.S. Application Data

(60) Provisional application No. 60/747,491, filed on May 17, 2006.

(51) Int. Cl.
*A61L 9/12* (2006.01)
*A61L 9/04* (2006.01)
*A45D 40/04* (2006.01)
*G01F 11/00* (2006.01)

(52) U.S. Cl. ............... 239/35; 239/54; 239/60; 239/71; 401/55; 401/68; 401/75; 222/390

(58) Field of Classification Search .......... 239/34, 239/35, 53–55, 57, 58, 60, 71, 73, 74, 6; 222/333, 386, 390; 401/55, 68, 171–176, 401/75
See application file for complete search history.

(56) References Cited

U.S. PATENT DOCUMENTS

| | | | | |
|---|---|---|---|---|
| 2,797,844 A * | 7/1957 | Meek | ............ | 239/58 |
| 3,946,945 A * | 3/1976 | Odioso et al. | ............ | 239/58 |
| 4,523,717 A * | 6/1985 | Schwab | ............ | 239/56 |
| 5,289,835 A * | 3/1994 | Harlan et al. | ............ | 132/313 |
| 5,538,161 A * | 7/1996 | Koehler et al. | ............ | 222/46 |
| 6,022,163 A * | 2/2000 | Asfur | ............ | 401/175 |
| 6,592,278 B1* | 7/2003 | Holthaus | ............ | 401/66 |
| 6,695,510 B1* | 2/2004 | Look et al. | ............ | 401/68 |
| 6,966,500 B1* | 11/2005 | Kelley | ............ | 239/60 |
| 2004/0188535 A1* | 9/2004 | Hart et al. | ............ | 239/57 |

* cited by examiner

*Primary Examiner*—Darren W Gorman
(74) *Attorney, Agent, or Firm*—Snell & Wilmer L.L.P.

(57) ABSTRACT

An air freshener with a device configured to maintain an air freshener's ability to disseminate a constant odor to an environment. The device incrementally advances the position of an air freshening composition such that an effective amount to maintain the air freshening odor is consistently exposed to the surrounding environment.

8 Claims, 5 Drawing Sheets

ACTUATED AIR FRESHENER DISPENSER

CROSS-REFERENCE TO RELATED APPLICATION

This Application claims priority to and the benefit of U.S. Provisional Patent Application No. 60/747,491 filed May 17, 2006 entitled "Actuated Air Freshener Dispenser," wherein such provisional application is hereby incorporated in its entirety, by reference.

FIELD OF INVENTION

The invention relates to a device for distributing an air freshener composition. More particularly, the device of the present invention comprises an actuated air freshener distribution device configured to advance the position of an air freshener composition so that an effective amount is continuously exposed to an environment.

BACKGROUND OF THE INVENTION

Air fresheners have long been common household items used to enhance the environment of their surrounding area. Many air fresheners comprise a fragranced liquid or gelatinous material which evaporate over time at room temperature or when heat is applied to them. These liquid or gelatinous materials are known as "volatiles."

Generally, a consumer purchases an air freshener, removes it from the packaging, and sets it in the desired location. The consumer can then enjoy the benefits of an odor enhanced environment. Once the air freshening volatiles have exhausted, though, the user must purchase another air freshener device for replacement. As such, the user is required to monitor the air freshener device and, upon identifying that the device has exhausted its volatiles, must purchase the replacement. Additionally, air fresheners are inconsistent in their ability to maintain a constant intensity of air freshness to their respective environment. For example, as the various volatiles that comprise the air freshening composition evaporate, they usually do so at varying rates, thereby resulting in an ever decreasing effectiveness to deliver adequate air freshness over the life of the air freshener.

What is needed is an air freshening device that is consistent in its ability to deliver a consistent level of air freshening intensity over the usable life of the air freshening device. Also needed is a device that has a usable life in excess of a typical air freshener, such that a user does need to monitor the device to the extent they would need to monitor a typical air freshener.

SUMMARY OF THE INVENTION

As set forth in the detailed description and accompanying figures, the present invention comprises, in various exemplary embodiments, a device configured to overcome a typical air freshener's shortcomings with regard to maintaining consistent odor effectiveness during the usable life of the product. As a result, an air freshener device that exhibits a useful life in excess of a typical air freshener is disclosed.

In accordance with an exemplary embodiment of the present invention, an air freshener is configured with an actuation mechanism that advances the position of an air freshener composition. In accordance with another aspect of the invention, the actuation mechanism of the air freshener is powered by at least one of a battery, solar cell, outlet plug, charged capacitor, and any like components that can provide operating power to the mechanism or cause the mechanism to actuate. Further, in accordance with another exemplary embodiment, the air freshening device is configured to exhibit a usable life in excess of typical static air fresheners.

BRIEF DESCRIPTION OF THE DRAWINGS

The subject invention will hereinafter be described in conjunction with the appended drawing figures, wherein like numerals denote like elements, and wherein.

DETAILED DESCRIPTION

The detailed description of various exemplary embodiments of the invention herein makes reference to the accompanying figures. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation.

In accordance with various exemplary embodiments of the present invention, an air freshener device is configured with an actuating mechanism that advances the position of an air freshener composition to expose a portion of the air freshening composition to an environment. In an exemplary embodiment of the present invention, an air freshener composition having a substantially solid or semi-solid form is provided, wherein the form is advanced by an actuation mechanism suitably connected to a motor. As the motor operates, it actuates the mechanism to incrementally advance the position of the air freshening composition. As the composition is advanced, a portion is exposed to the environment. The portion of the air freshening composition exposed to the environment evaporates depending on the certain environmental conditions such as temperature and humidity.

In this exemplary embodiment, a portion of the air freshening composition is continually exposed to the environment. Specifically, a portion of air freshening composition is exposed to the environment and evaporates. Before the portion of the composition completely evaporates, the air freshening composition is advanced by the motor and actuation mechanism. exposing a new un-evaporated portion of the composition to the environment. Therefore, a portion of the air freshening composition is always exposed to the environment until the air freshening composition completely evaporates or is otherwise volitized.

Figure 1:
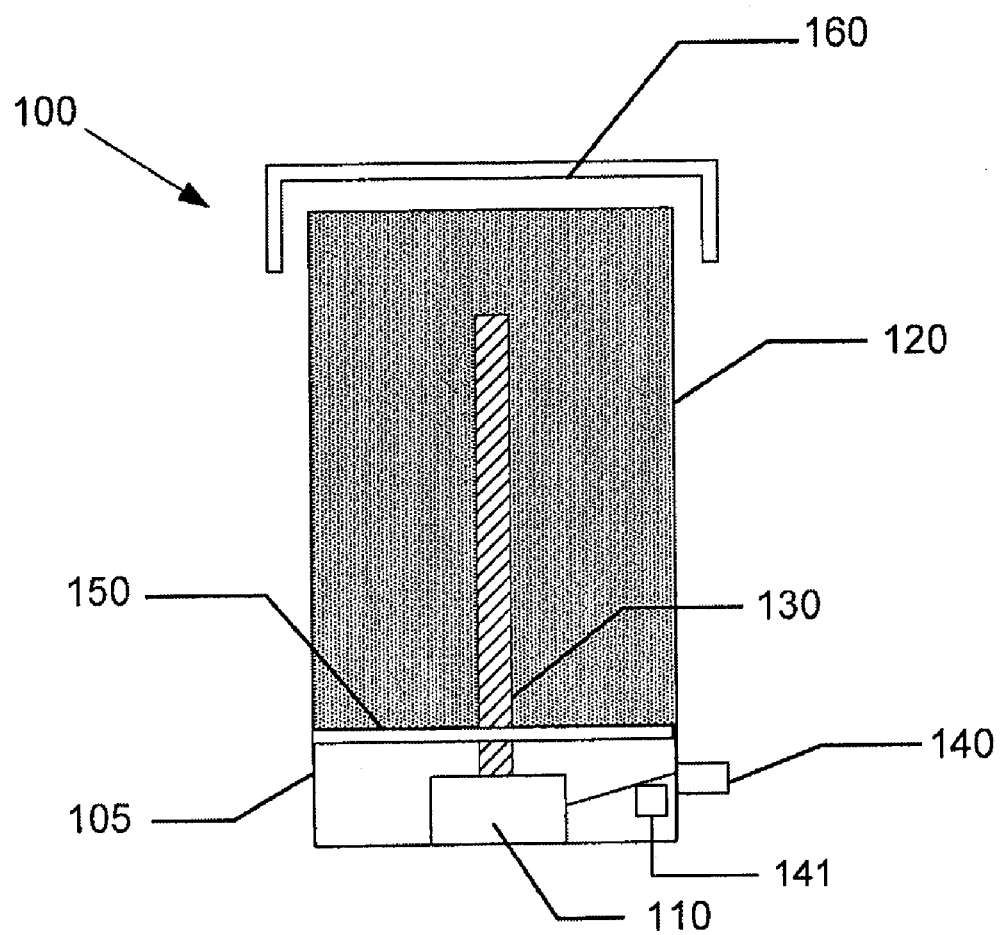
FIG. 1 is an schematic diagram of the present invention depicting a motorized air freshening device in a pre-actuated state in an exemplary embodiment.

In accordance with an exemplary embodiment of the present invention and with reference to FIG. 1, an actuatable air freshener is shown. Air freshener 100 comprises a vessel 105 to house various components of air freshener 100 such as an actuating mechanism 110 and a composition 120 which is scented. Actuating mechanism 110 comprises various elements that function to incrementally advance the position of composition 120.

In an exemplary embodiment, an actuating mechanism 110 is operable by a switch 140 to actuate an advancing platform 150 by an advancing member such as a screw 130. The motor drives screw 130 which moves composition 120 into or out of the environment depending on the direction that screw 130 moves. In other exemplary embodiments, the motor is eliminated and the screw 130 is moved by a dial, knob, or other type of user-controlled device located on air freshener 100.

Figure 2:
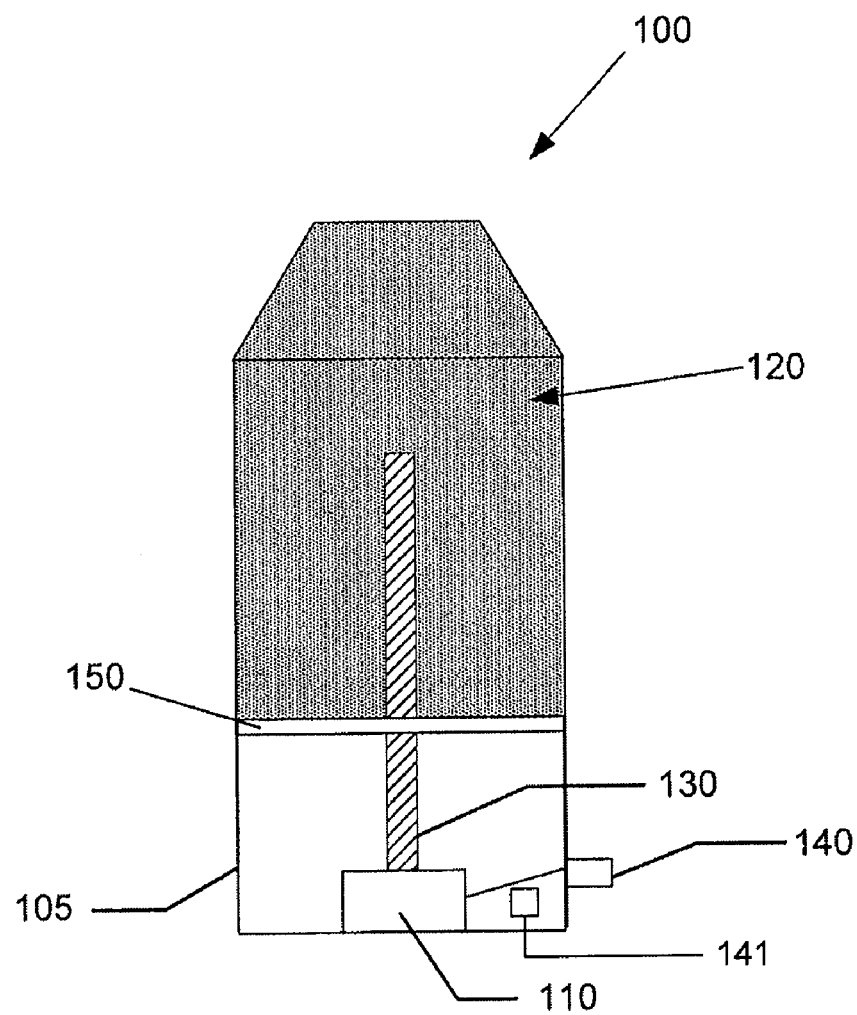
FIG. 2 is an schematic diagram of the present invention depicting the motorized air freshening device in the actuated state, wherein the air freshening composition is shown in an advanced position and exposed to the environment in an exemplary embodiment.

In the exemplary embodiment depicted in FIG. 1, advancing platform 150 is configured to support composition 120, and as screw 130 is turned by the motor advancing platform 150 pushes composition 120 into the environment. FIG. 2. depicts composition 120 in an advanced state, wherein a portion is exposed to the environment.

In other exemplary embodiments, advancing platform 150 can be operated by other components than depicted in FIG. 1. For example, advancing platform 150 can be raised and lowered by a piston or similar mechanism. In yet other exemplary embodiments, air advancing platform 150 is driven by pins. Further, while only a single screw 130 is depicted, a plurality of mechanisms could be used to move advancing platform 150 as noted below.

Alternatively, advancing platform 150 may not be mechanically driven but operated by the user. In such an exemplary embodiment, advancing platform 150 may contact vessel 105 by friction fit or contact vessel 105 by interlocking releasable members such as tabs (not shown). In this exemplary embodiment, a user can manually advance platform 150 with their hands or other object.

In yet other exemplary embodiments, advancing platform 150 may not move at all but rather is stationary. In these exemplary embodiments, vessel 105 may be movable by a sliding, twisting, or other similar motion that exposes composition 120 to the environment. Moving the vessel 105 exposes composition 120 to the environment thereby freshening the air in the surrounding environment. In still yet another exemplary embodiment, vessel 105 comprises a material that is easily removable and allows the user to remove a portion of vessel 105 to expose composition 120 to the environment. In this exemplary embodiment, vessel 105 may be constructed from a paper-based material such as cardboard or any other type of material that is easily removable.

In accordance with an aspect of the invention, vessel 105 comprises any configuration that houses the various actuating elements and allows composition 120 to be stored and subsequently incrementally advanced within vessel 105 to expose a portion of composition 120 to the environment. In one exemplary embodiment, vessel 105 comprises a regular geometric tubular shape such as, for example, an oval, circle, rectangle, square, or any other polygonal shape. In other exemplary embodiments, vessel 105 comprises other configurations, such as irregular shapes or decorative shapes.

Figure 4:
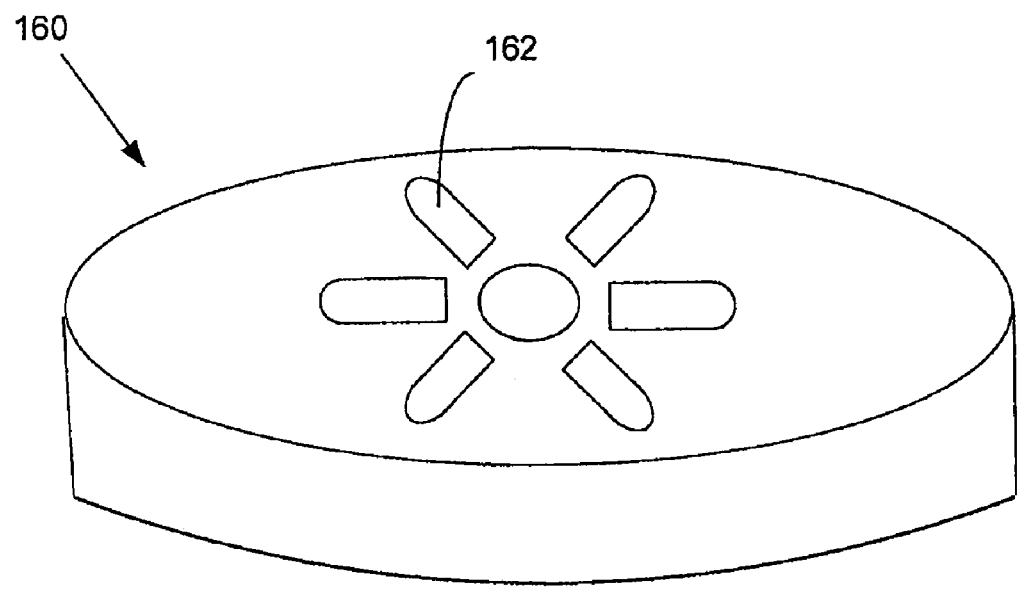
FIG. 4 is a schematic diagram depicting a cap with an opening according to an exemplary embodiment of the present invention.

In accordance with various embodiments of the invention, cap 160, is used to seal vessel 105. As cap 160 is removed actuating mechanism 110 may be activated and composition 120 can advance and, thereby, become exposed to the environment, as shown in FIG. 2. In another aspect of the invention, a cap 160 may be used as to facilitate a decorative exposed shape to provide a more aesthetically pleasing embodiment. For example, instead of air freshener 100 displaying exposed composition 120 as composition 120 emerges from vessel 105, cap 160, as the one shown in FIG. 1 further comprises an opening 162 as shown in FIG. 4. Other openings 162 other than shown in FIG. 4. can be used for cap 160 and fall within the scope of the present invention though. In this exemplary embodiment, as composition 120 is advanced, it is forced through opening 162 of cap 160, and the exposed air freshening composition emerges as a 3-D decorative design.

In accordance with yet another aspect of the invention, cap 160 may be used as both an opening 162 and a sealing element. In one exemplary embodiment, cap 160 may comprise a peel-off cover, such that upon removal, air freshener 100 can be activated and composition 120 can be exposed to the environment. In another exemplary embodiment, cap 160 may screw onto air freshener 100 or snap onto air freshener 100.

In accordance with one exemplary embodiment of the present invention, air freshener 100 comprises actuating mechanism 110 which comprises advancing platform 150 and screw 130. As illustrated in FIGS. 1 and 2, the motor is powered by a battery. However, it should be appreciated by those skilled in the art that the motor may comprise other elements configured to supply power to the motor. For example, power may be supplied by elements such as, a solar cell, a charged capacitor, an outlet plug, gravity, and any like components that can provide operating power to the motor and associated actuating mechanism 110. With return reference to FIG. 2, as composition 120 advances due to the operation of actuating mechanism 110 and is exposed to the environment, composition 120 evaporates or is otherwise volatized at a particular rate dictated by the particular air freshening composition and the encountered environmental factors.

In an exemplary embodiment of the present invention, air freshener 100 comprises a switch that is suitably configured to initiate the operation of actuating mechanism 110. The switch allows a user to control when air freshener 100 is actuated. For example, the switch is in an "OFF" position during shipping and display. Once a consumer purchases the item, it is removed from the packaging and the switch is turned to the "ON" position, thereby actuating the unit. The switch also allows the user to control the operation of air freshener 100 based upon their particular lifestyle. For example, if a user travels frequently or opts to be away from the environment, the user has the ability to disengage operation of the unit by turning the switch to the OFF position. With reference to the FIGS. 1 and 2, air freshener 100 further comprises switch 140 suitably connected to actuating mechanism 110. As switch 140 is set to the ON position, air freshener 100 is actuated, when set in the OFF position, actuating mechanism 110 is deactivated.

Figure 3A:
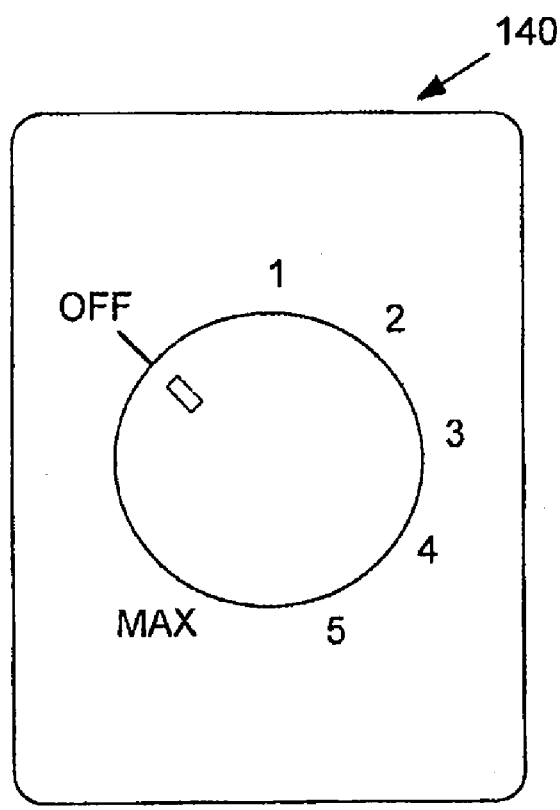
FIG. 3A is a schematic diagram depicting a discrete switch for operating the device according to an exemplary embodiment.
Figure 3B:
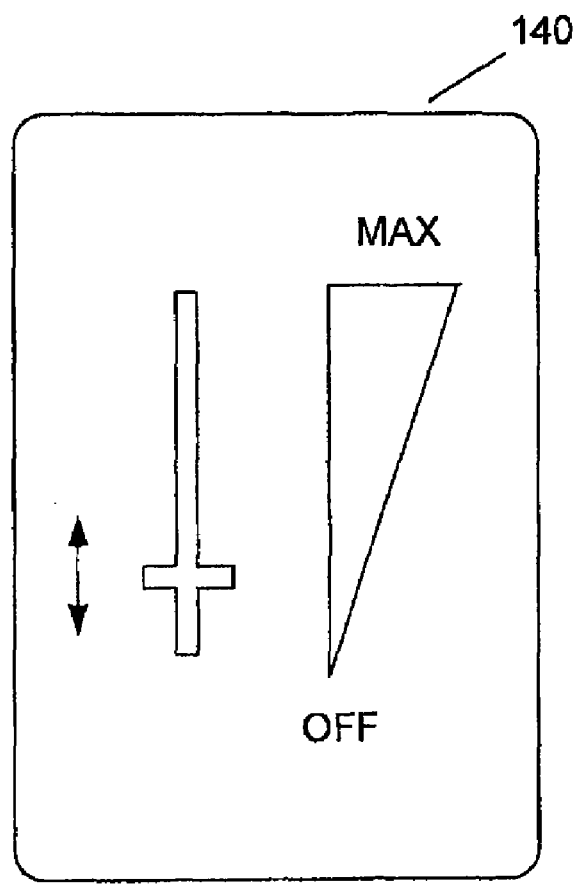
FIG. 3B is a schematic diagram depicting a variable switch for operating the device according to an exemplary embodiment of the present invention.

In one exemplary embodiment of the present invention, switch 140 is configured to be adjustable and allows for gradients of operability of actuating mechanism 110. In this embodiment, switch 140 comprises a discrete or variable control mechanism. In other exemplary embodiments, switch 140 merely acts as an "on/off" switch. With reference to FIG. 3A, an exemplary discrete switch 140 is depicted, wherein the device may be adjusted from an OFF position (i.e. no power or movement) to variable discrete operating positions (1-5) up to a MAX position (i.e. full power and movement). With reference to FIG. 3B, an exemplary variable switch 140 is depicted, wherein the air freshener 100 may be adjusted to operate along any point between the OFF and MAX position.

By incorporating such switches, a user can synchronize the optimum operating parameter for their unique environmental conditions, or tailor the device to their operating preferences.

In accordance with yet another aspect of the present invention, switch 140 is configured to be suitably connected to elements that further facilitate control of actuating mechanism 110. For example, switch 140 may be suitably connected to a control/timing device that is configured to monitor various control elements and/or temporal conditions. As the control device is programmed by a user or encounters pre-set conditions, the control device feeds input into switch 140 (or directly to the motor) to subsequently control operation of actuating mechanism 110.

For example, switch 140 may be configured to operate in conjunction with an environmental monitoring device 141 which is configured to monitor various conditions either in the surrounding environment or within air freshener 100. A user, knowing that the evaporation rate of composition 120 may be dependent upon particular environmental conditions, such as, air temperature, pressure, moisture content, or the like, benefits from the monitoring device 141 that forwards a signal to switch 140 so that switch 140 can adjust the setting of air freshener 100 to appropriately maintain the optimum setting. In other exemplary embodiments of the present invention, switch 140 merely acts as a timing device. In these exemplary embodiments, switch 140 may be turned to a pre-set time amount and activate actuating mechanism 110 for desired time period.

In various exemplary embodiments of the present invention, actuating mechanism 110 comprises a motor, a screw 130, and an advancing platform 150. As described briefly herein, composition 120 is supported by advancing platform 150. As actuating mechanism 110 is engaged to operate by switch 140, the motor turns screw 130, thereby causing advancing platform 150 to rise, and consequently causing composition 120 to emerge from vessel 105 and become exposed to the environment.

It should be appreciated by those skilled in the art that screw 130 and advancing platform 150 is merely one example of an actuation configuration. Any other configuration that provides for advancement of composition 120 by a powering means, such as a motor, is contemplated by the present invention. For example, air freshener 100 may benefit from a configuration upside down, and advancing the composition occurs through gravity and a braking mechanism. Moreover, the actuation configuration may comprise any other known combination of screws, platforms, pulleys, cables, wedges, compressed air, gears, bearings, rods, and any like actuating elements or advancing members. In this regard, any other advancing member or device that performs the function of screw 130 can be used and fall within the scope of the present invention.

In an exemplary embodiment of the present invention, air freshener 100 comprises composition 120 that is volatizable and evaporates based on environmental conditions. As used throughout this application, the term "volatizable" means the ability for the composition 120 to emit a sufficient amount of fragrance to adequately freshen the surrounding environment whether or not it is evaporated. For example, a solid or gelatinous composition 120 may be "volatized" if it has lost its ability to emit a fragrance sufficient to freshen the surrounding environment. Therefore, a portion of this type of composition 120 may protrude from the air freshener 100 and would be volatized if that portion no longer emitted a sufficient amount of fragrance to freshen the air. Further, the term "volatized" also means when composition 120 is evaporating or is completely evaporated.

Composition 120 comprises a gel form in one exemplary embodiment. In other exemplary embodiments, composition 120 may be configured with any consistency such that upon exposure to the environment, composition 120 is able to maintain a static position. In other words, composition 120 is sturdy enough to remain in one position, supported by a platform, such that composition 120 may interact with the natural fluid flow of the air when exposed to the environment. In accordance with various exemplary embodiments of the present invention, composition 120 may comprise various configurations and may be a liquid, solid, gelatinous, or take other states.

For example, composition 120 may comprise at least two different scents that, in one instance, are layered, thus, as composition 120 advances, as one scent is exhausted over time, the other scent is exposed. In another example, composition 120 comprises various aesthetic characteristics, for example, color. For example, composition 120 may comprise two or more different colors that again may be layered, and as composition 120 advances, a new color is exposed.

In accordance with another aspect of the present invention, composition 120 may be configured to indicate when the life of air freshener 100 or composition 120 is exhausted. As illustrated by FIGS. 1 and 2, because the device is configured to consistently expose a portion of composition 120 to the environment, a user may have a difficult time determining how much longer the device will last before it must be replaced. In one exemplary embodiment, vessel 105 may be transparent or have a transparent portion to allow the user to see to what level composition 120 has advanced and exhausted.

In another exemplary embodiment, composition 120 may comprise a separate color towards the last portion to be exposed. In this manner, a user can identify that air freshener 100 must be replaced or refilled upon noticing the change in color that is exposed. The same type of indication can be accomplished by other indicators, such as a separate odor. In yet another exemplary embodiment, advancing platform 150, as it advances incrementally, may be configured to actuate an end of use indicator switch. The indicator switch, for example, may comprise an indicator light, or audible indicator.

Finally, various principles of the invention have been described in illustrative embodiments. However, many combinations and modifications of the above-described structures, arrangements, proportions, elements materials and components, used in the practice of the invention, in addition to those not specifically described, can be varied without departing from those principles.

I claim:

1. An air freshener comprising: a vessel; an advancing platform disposed within the vessel; an advancing member connected to the advancing platform configured to move the advancing platform; a motor connected to and driving the advancing member; an environmental monitoring device configured to control operation of the motor; a solid or semi-solid air freshening composition supported by the advancing platform; and a porous cap attached to the vessel and configured to allow the air freshening composition to pass through the cap.

2. The air freshener of claim 1, further comprising an indicator to indicate the amount of air freshening composition contained within the air freshener.

3. The air freshener of claim 2, wherein the indicator comprises a color applied to at least a portion of the air freshening composition.

4. The air freshener of claim 2, wherein the indicator comprises a transparent surface located on the vessel.

5. An air freshener comprising: a vessel; an actuating mechanism within the vessel comprising an advancing platform, a screw connected to the advancing platform, and a motor driving the screw wherein the motor is controlled by a timing mechanism; a solid or semi-solid volatizable air freshening composition resting on the advancing platform wherein part of the volatizable air freshening composition is confined within the vessel and part of the volatizable air freshening composition is exposed to an environment outside of the vessel; and an indicator to indicate the amount of volatizable air freshening composition contained within the air freshener, wherein the indicator comprises a color applied to at least a portion of the air freshening composition.

6. The air freshener of claim 5, further comprising a cap attached to the vessel.

7. The air freshener of claim 6, wherein the cap comprises an opening to allow the air freshening composition to pass through the cap.

8. The air freshener of claim 5, wherein the indicator comprises a transparent surface located on the vessel.

* * * * *